US010064828B1

(12) United States Patent
Odidi et al.

(10) Patent No.: US 10,064,828 B1
(45) Date of Patent: Sep. 4, 2018

(54) PULSED EXTENDED-PULSED AND EXTENDED-PULSED PULSED DRUG DELIVERY SYSTEMS

(75) Inventors: Isa Odidi, Toronto (CA); Amina Odidi, Toronto (CA)

(73) Assignee: INTELLIPHARMACEUTICS CORP., Toronto (CA)

( * ) Notice: Subject to any disclaimer, the term of this patent is extended or adjusted under 35 U.S.C. 154(b) by 683 days.

(21) Appl. No.: 11/315,868

(22) Filed: Dec. 23, 2005

(51) Int. Cl.
| *A61K 9/22* | (2006.01) |
| *A61K 9/52* | (2006.01) |
| *A61K 31/138* | (2006.01) |
| *A61K 31/135* | (2006.01) |
| *A61K 31/145* | (2006.01) |
| *A61K 9/20* | (2006.01) |
| *A61K 9/48* | (2006.01) |

(52) U.S. Cl.
CPC .......... *A61K 9/4816* (2013.01); *A61K 9/2004* (2013.01); *A61K 31/135* (2013.01); *A61K 31/138* (2013.01); *A61K 31/145* (2013.01)

(58) Field of Classification Search
None
See application file for complete search history.

(56) References Cited

U.S. PATENT DOCUMENTS

| 2,540,979 A | 2/1951 | MacDonnell |
| 3,254,088 A | 5/1966 | Juda et al. |
| 3,493,657 A | 2/1970 | Lewenstein |
| 3,629,393 A | 12/1971 | Nakamoto et al. |
| 3,728,445 A | 4/1973 | Bardani |
| 3,773,955 A | 11/1973 | Pachter |
| 3,789,117 A | 1/1974 | Tsujino |
| 3,819,706 A | 6/1974 | Mehta |
| 3,845,770 A | 11/1974 | Higuchi |
| 3,856,721 A | 12/1974 | Fritschel |
| 3,916,899 A | 11/1975 | Theeuwes et al. |
| 4,008,719 A | 2/1977 | Theeuwes |
| 4,016,880 A | 4/1977 | Theeuwes |
| 4,034,758 A | 7/1977 | Theeuwes |
| 4,036,228 A | 7/1977 | Theeuwes |
| 4,045,563 A | 8/1977 | Berntsson et al. |
| 4,060,598 A | 11/1977 | Groppenbacher et al. |
| 4,077,407 A | 3/1978 | Theeuwes |
| 4,160,452 A | 7/1979 | Theeuwes |
| 4,161,477 A | 7/1979 | Long |
| 4,183,838 A | 1/1980 | Gagliani |
| 4,183,839 A | 1/1980 | Gagliani |
| 4,193,985 A | 3/1980 | Bechgaard |
| 4,200,098 A | 4/1980 | Ayer |
| 4,218,433 A | 8/1980 | Kooichi et al. |
| 4,248,856 A | 2/1981 | Guley et al. |
| 4,250,136 A | 2/1981 | Rex |
| 4,252,786 A | 2/1981 | Weiss et al. |
| 4,255,431 A | 3/1981 | Junggren et al. |
| 4,309,405 A | 1/1982 | Guley et al. |
| 4,327,725 A | 5/1982 | Cortese |
| 4,330,338 A | 5/1982 | Banker |
| 4,337,257 A | 6/1982 | Junggren |
| 4,389,393 A | 6/1983 | Schor et al. |
| 4,425,441 A | 1/1984 | Gagliani et al. |
| 4,457,933 A | 7/1984 | Gordon |
| 4,461,759 A | 7/1984 | Dunn |
| 4,486,412 A | 12/1984 | Shah et al. |
| 4,508,905 A | 4/1985 | Junggren |
| 4,514,538 A | 4/1985 | Shvakhman et al. |
| 4,517,112 A | 5/1985 | Mardis et al. |
| 4,518,717 A | 5/1985 | Long et al. |
| 4,545,412 A | 10/1985 | Gamberini |
| 4,582,835 A | 4/1986 | Lewis |
| 4,606,909 A | 8/1986 | Bechgaard |
| 4,610,870 A | 9/1986 | Jain et al. |
| 4,612,008 A | 9/1986 | Wong et al. |
| 4,628,098 A | 12/1986 | Nohara et al. |
| 4,666,705 A | 5/1987 | DeCrosta et al. |
| 4,676,929 A | 6/1987 | Rittler |
| 4,684,516 A | 8/1987 | Bhutani |
| 4,686,230 A | 8/1987 | Rainer et al. |
| 4,689,333 A | 8/1987 | Nohara et al. |
| 4,704,285 A | 11/1987 | Alderman |
| 4,708,834 A | 11/1987 | Cohen et al. |
| 4,713,248 A | 12/1987 | Kjomaes et al. |
| 4,756,911 A | 7/1988 | Drost et al. |
| 4,758,579 A | 7/1988 | Kohl et al. |
| 4,765,989 A | 8/1988 | Wong et al. |
| 4,783,337 A | 11/1988 | Wong et al. |
| 4,786,505 A | 11/1988 | Lovgren et al. |
| 4,812,446 A | 3/1989 | Brand |
| 4,818,760 A | 4/1989 | Binder et al. |
| 4,832,958 A | 5/1989 | Baudier et al. |
| 4,844,905 A | 7/1989 | Ichikawa et al. |
| 4,845,118 A | 7/1989 | Lang et al. |
| 4,851,228 A | 7/1989 | Zentner et al. |
| 4,853,230 A | 8/1989 | Lovgren et al. |
| 4,869,908 A | 9/1989 | Kirschner et al. |
| 4,880,631 A | 11/1989 | Haslam |
| 4,886,668 A | 12/1989 | Haslam |
| 4,891,223 A | 1/1990 | Ambegaonkar et al. |

(Continued)

FOREIGN PATENT DOCUMENTS

| CA | 2286684 A1 | 10/1998 |
| CA | 2529984 A1 | 12/2004 |

(Continued)

OTHER PUBLICATIONS

Merriam-Webster Online Dictionary, http://www.meriam-webster.com/dictionar/prevent, obtained online Feb. 8, 2008.*

(Continued)

*Primary Examiner* — Abigail Vanhorn
(74) *Attorney, Agent, or Firm* — Thomas Horstemeyer, LLP (57) ABSTRACT

The disclosure is directed to drug delivery devices that provide for combinations of extended and pulsed controlled release delivery of active pharmaceutical ingredient(s) APIs. The described drug delivery devices for oral administration of therapeutic compositions can include two or more populations of unit dosage forms including one or more API's in various combinations of pulsed and delayed/extended delivery formulations. The population of unit dosage forms are provided in a variety of different vehicles such as granules, beads, pellets, or tablets and can be contained within a drug delivery device of the present disclosure.

41 Claims, 7 Drawing Sheets

(56) References Cited

U.S. PATENT DOCUMENTS

| | | | | |
|---|---|---|---|---|
| 4,892,742 A | | 1/1990 | Shah | |
| 4,900,557 A | | 2/1990 | Dell et al. | |
| 4,904,476 A | | 2/1990 | Mehta et al. | |
| 4,927,640 A | | 5/1990 | Dahlinder et al. | |
| 4,935,243 A | | 6/1990 | Borkan et al. | |
| 4,940,587 A | | 7/1990 | Jenkins et al. | |
| 4,940,588 A | | 7/1990 | Sparks et al. | |
| 4,946,853 A | | 8/1990 | Bannon et al. | |
| 4,963,365 A | | 10/1990 | Samejima et al. | |
| 4,965,269 A | | 10/1990 | Brandstrom et al. | |
| 4,966,768 A | | 10/1990 | Michelucci et al. | |
| 5,000,962 A | | 3/1991 | Sangekar et al. | |
| 5,004,614 A | | 4/1991 | Staniforth | |
| 5,021,433 A | | 6/1991 | Alminger et al. | |
| 5,028,434 A | | 7/1991 | Barclay et al. | |
| 5,045,552 A | | 9/1991 | Souda et al. | |
| 5,049,394 A | | 9/1991 | Howard et al. | |
| 5,071,643 A | | 12/1991 | Yu et al. | |
| 5,073,384 A | | 12/1991 | Valentine et al. | |
| 5,077,051 A | | 12/1991 | Gallopo | |
| 5,123,146 A | | 6/1992 | Olson | |
| 5,149,702 A | | 9/1992 | Yamada et al. | |
| 5,190,763 A | | 3/1993 | Edgren et al. | |
| 5,202,128 A | | 4/1993 | Morella et al. | |
| 5,219,572 A | | 6/1993 | Sivaramakrishnan | |
| 5,229,131 A | * | 7/1993 | Amidon et al. | 424/451 |
| 5,236,714 A | | 8/1993 | Lee et al. | |
| 5,240,712 A | | 8/1993 | Smith | |
| 5,252,339 A | | 10/1993 | Cristofori et al. | |
| 5,260,069 A | | 11/1993 | Chen | |
| 5,286,497 A | | 2/1994 | Hendrickson et al. | |
| 5,288,500 A | | 2/1994 | Ibsen | |
| 5,290,816 A | | 3/1994 | Blumberg | |
| 5,330,766 A | | 7/1994 | Morella et al. | |
| 5,376,388 A | | 12/1994 | Meyers | |
| 5,378,474 A | | 1/1995 | Morella et al. | |
| 5,393,528 A | | 2/1995 | Staab | |
| 5,415,871 A | | 5/1995 | Pankhania et al. | |
| 5,425,950 A | | 6/1995 | Dandiker et al. | |
| 5,430,042 A | | 7/1995 | Lindberg et al. | |
| 5,445,829 A | | 8/1995 | Paradissis et al. | |
| 5,458,887 A | | 10/1995 | Chen et al. | |
| 5,472,711 A | | 12/1995 | Baichwal | |
| 5,480,335 A | | 1/1996 | Caveza | |
| 5,503,846 A | * | 4/1996 | Wehling et al. | 424/466 |
| 5,508,040 A | | 4/1996 | Chen | |
| 5,527,545 A | | 6/1996 | Santus et al. | |
| 5,595,762 A | | 1/1997 | Derrieu | |
| 5,681,581 A | | 10/1997 | Dunn | |
| 5,708,017 A | | 1/1998 | Dave et al. | |
| 5,713,000 A | | 1/1998 | Larson | |
| 5,736,159 A | | 4/1998 | Chen et al. | |
| 5,753,265 A | | 5/1998 | Bergstrand | |
| 5,759,577 A | | 6/1998 | Barcomb | |
| 5,760,121 A | | 6/1998 | Beall et al. | |
| 5,780,055 A | | 7/1998 | Habib et al. | |
| 5,783,215 A | | 7/1998 | Arwidsson et al. | |
| 5,795,583 A | | 8/1998 | Grune et al. | |
| 5,800,422 A | | 9/1998 | Dong et al. | |
| 5,817,338 A | | 10/1998 | Bergstrand | |
| 5,840,329 A | | 11/1998 | Bai | |
| 5,840,910 A | | 11/1998 | Souda et al. | |
| 5,879,708 A | | 3/1999 | Makino et al. | |
| 5,955,106 A | | 9/1999 | Moeckel et al. | |
| 5,972,329 A | | 10/1999 | Chuang et al. | |
| 5,998,445 A | | 12/1999 | Souda et al. | |
| 6,022,562 A | | 2/2000 | Autant et al. | |
| 6,039,975 A | | 3/2000 | Shah et al. | |
| 6,046,177 A | | 4/2000 | Stella et al. | |
| 6,068,853 A | | 5/2000 | Giannos et al. | |
| 6,068,856 A | | 5/2000 | Sachs et al. | |
| 6,090,401 A | | 7/2000 | Gowan et al. | |
| 6,099,859 A | | 8/2000 | Cheng et al. | |
| 6,106,864 A | | 8/2000 | Dolan et al. | |
| 6,183,776 B1 | | 2/2001 | Depui et al. | |
| 6,183,777 B1 | | 2/2001 | Chen et al. | |
| 6,194,001 B1 | | 2/2001 | Gribbon et al. | |
| 6,210,710 B1 | | 4/2001 | Skinner | |
| 6,228,400 B1 | | 5/2001 | Lee et al. | |
| 6,251,432 B1 | | 6/2001 | Mazer et al. | |
| 6,261,582 B1 | | 7/2001 | Needham et al. | |
| 6,270,804 B1 | | 8/2001 | Getz et al. | |
| 6,296,876 B1 | | 10/2001 | Odidi et al. | |
| 6,312,723 B1 | | 11/2001 | Whittle et al. | |
| 6,312,724 B1 | | 11/2001 | Odidi et al. | |
| 6,368,635 B1 | | 4/2002 | Akiyama et al. | |
| 6,433,040 B1 | | 8/2002 | Dellamary et al. | |
| 6,479,075 B1 | | 11/2002 | Odidi et al. | |
| 6,489,346 B1 | | 12/2002 | Phillips | |
| 6,491,949 B2 | | 12/2002 | Faour et al. | |
| 6,509,037 B2 | | 1/2003 | Odidi | |
| 6,527,051 B1 | | 3/2003 | Reddy et al. | |
| 6,555,127 B2 | | 4/2003 | Steiner | |
| 6,558,704 B1 | | 5/2003 | Bartholomaeus et al. | |
| 6,569,453 B2 | | 5/2003 | Linder et al. | |
| 6,599,529 B1 | | 7/2003 | Skinhoj | |
| 6,605,300 B1 | * | 8/2003 | Burnside et al. | 424/452 |
| 6,607,751 B1 | | 8/2003 | Odidi et al. | |
| 6,627,635 B2 | | 9/2003 | Palermo et al. | |
| 6,645,524 B2 | * | 11/2003 | Midha et al. | 424/459 |
| 6,645,528 B1 | | 11/2003 | Straub et al. | |
| 6,645,988 B2 | | 11/2003 | Phillips | |
| 6,652,882 B1 | | 11/2003 | Odidi et al. | |
| 6,673,367 B1 | | 1/2004 | Goldenheim et al. | |
| 6,676,966 B1 | | 1/2004 | Odidi et al. | |
| 6,696,088 B2 | | 2/2004 | Oshlack et al. | |
| 6,699,885 B2 | | 3/2004 | Phillips | |
| 6,780,882 B2 | | 8/2004 | Phillips | |
| 6,800,668 B1 | | 10/2004 | Odidi et al. | |
| 6,902,742 B2 | | 6/2005 | Devane et al. | |
| 6,911,217 B1 | | 6/2005 | Gren et al. | |
| 6,946,146 B2 | | 9/2005 | Mulye | |
| 6,991,804 B2 | | 1/2006 | Helmus et al. | |
| 7,090,867 B2 | | 8/2006 | Odidi et al. | |
| 7,135,465 B2 | | 11/2006 | Abramowitz et al. | |
| 7,157,103 B2 | | 1/2007 | Sackler | |
| 7,858,119 B1 | | 12/2010 | Odidi et al. | |
| 7,906,143 B1 | | 3/2011 | Odidi et al. | |
| 9,078,827 B2 | | 7/2015 | Odidi et al. | |
| 2001/0006649 A1 | | 7/2001 | Chen | |
| 2002/0002147 A1 | | 1/2002 | Abramowitz et al. | |
| 2002/0045646 A1 | | 4/2002 | Phillips | |
| 2002/0064099 A1 | | 5/2002 | Wyssbrod et al. | |
| 2002/0086885 A1 | | 7/2002 | Odaka et al. | |
| 2002/0110590 A1 | | 8/2002 | Shaked et al. | |
| 2002/0128293 A1 | | 9/2002 | Rampal et al. | |
| 2002/0132005 A1 | | 9/2002 | Faour | |
| 2002/0150535 A1 | | 10/2002 | Madras et al. | |
| 2003/0064099 A1 | | 4/2003 | Oshlack et al. | |
| 2003/0064101 A1 | | 4/2003 | Mehta et al. | |
| 2003/0068370 A1 | | 4/2003 | Sackler | |
| 2003/0068371 A1 | | 4/2003 | Oshlack et al. | |
| 2003/0077297 A1 | * | 4/2003 | Chen et al. | 424/400 |
| 2003/0118641 A1 | | 6/2003 | Maloney et al. | |
| 2003/0118669 A1 | | 6/2003 | Phillips | |
| 2003/0185887 A1 | | 10/2003 | Chen et al. | |
| 2003/0215507 A1 | | 11/2003 | Sherman et al. | |
| 2003/0215527 A1 | | 11/2003 | Phillips | |
| 2003/0220413 A1 | | 11/2003 | Petereit et al. | |
| 2003/0235616 A1 | | 12/2003 | Sowden et al. | |
| 2004/0048896 A1 | | 3/2004 | Phillips | |
| 2004/0058018 A1 | | 3/2004 | Phillips | |
| 2004/0101558 A1 | | 5/2004 | Dietrich et al. | |
| 2004/0131669 A1 | | 7/2004 | Kerc | |
| 2004/0171646 A1 | | 9/2004 | Phillips | |
| 2004/0185093 A1 | * | 9/2004 | Szymczak | 424/451 |
| 2004/0198775 A1 | * | 10/2004 | Fraser et al. | 514/355 |
| 2004/0265370 A1 | * | 12/2004 | Odidi et al. | 424/452 |
| 2004/0265380 A1 | | 12/2004 | Delmas et al. | |
| 2005/0004171 A1 | | 1/2005 | Phillips | |
| 2005/0042304 A1 | | 2/2005 | Phillips | |
| 2005/0054682 A1 | | 3/2005 | Phillips | |
| 2005/0186268 A1 | | 8/2005 | Hoshi et al. | |
| 2005/0196436 A1 | | 9/2005 | Chantranukul et al. | |

(56) References Cited

U.S. PATENT DOCUMENTS

| | | | |
|---|---|---|---|
| 2005/0214373 A1 | 9/2005 | Desai et al. | |
| 2006/0003001 A1 | 1/2006 | Devane et al. | |
| 2006/0004193 A1 | 1/2006 | Muller | |
| 2006/0018948 A1 | 1/2006 | Guire et al. | |
| 2006/0024361 A1* | 2/2006 | Odidi et al. | 424/464 |
| 2006/0039864 A1 | 2/2006 | Bartholomaus | |
| 2006/0039976 A1* | 2/2006 | Odidi et al. | 424/472 |
| 2006/0099246 A1 | 5/2006 | Tanner et al. | |
| 2006/0017336 A1 | 6/2006 | Knauff | |
| 2006/0153909 A1 | 7/2006 | Motoune | |
| 2006/0205681 A1 | 9/2006 | Moaddeb | |
| 2007/0003619 A1 | 1/2007 | Smith | |
| 2007/0009589 A1 | 1/2007 | Raghupathi et al. | |
| 2007/0077293 A1 | 4/2007 | Park | |
| 2007/0104778 A1 | 5/2007 | Zeng et al. | |
| 2007/0131357 A1 | 6/2007 | Wu | |
| 2007/0166370 A1* | 7/2007 | Odidi et al. | 424/451 |
| 2007/0286902 A1 | 12/2007 | Xie et al. | |
| 2009/0220613 A1* | 9/2009 | Odidi et al. | 424/497 |

FOREIGN PATENT DOCUMENTS

| | | |
|---|---|---|
| CA | 2551946 | 7/2005 |
| CN | 1634116 A | 7/2005 |
| DE | 1204363 | 11/1965 |
| DE | 3943242 A1 | 6/1990 |
| DE | 3531487 C2 | 8/1995 |
| DE | 19635676 A1 | 3/1998 |
| EP | 0005129 B1 | 4/1981 |
| EP | 0157695 A2 | 9/1985 |
| EP | 0166287 B1 | 1/1986 |
| EP | 0174726 A1 | 3/1986 |
| EP | 0184322 B1 | 6/1986 |
| EP | 0234485 B1 | 9/1987 |
| EP | 080341 B1 | 10/1987 |
| EP | 0261478 A1 | 3/1988 |
| EP | 0268956 B1 | 6/1988 |
| EP | 0270305 A2 | 6/1988 |
| EP | 0342522 A1 | 11/1989 |
| EP | 0366321 A1 | 5/1990 |
| EP | 0403383 A1 | 12/1990 |
| EP | 0434999 B1 | 7/1991 |
| EP | 0453001 A1 | 10/1991 |
| EP | 0527638 A1 | 2/1993 |
| EP | 0797991 A1 | 10/1997 |
| EP | 0960620 A1 | 12/1999 |
| EP | 1017370 B1 | 7/2000 |
| EP | 1493435 | 1/2005 |
| EP | 1731142 A1 | 12/2006 |
| FR | 2419722 A1 | 10/1979 |
| FR | 2624012 | 6/1989 |
| FR | 2778848 | 11/1999 |
| GB | 2134516 A | 8/1984 |
| GB | 2163747 A | 3/1986 |
| HU | 203477 B | 1/1991 |
| JP | 2002-068964 | 3/2002 |
| JP | 2005500364 | 1/2005 |
| WO | WO8503436 A1 | 8/1985 |
| WO | WO8705212 A1 | 9/1987 |
| WO | WO9011070 A1 | 10/1990 |
| WO | WO9107950 A1 | 6/1991 |
| WO | WO9116885 A1 | 11/1991 |
| WO | WO9119710 A1 | 12/1991 |
| WO | WO9204013 A1 | 3/1992 |
| WO | WO9208716 A1 | 5/1992 |
| WO | WO9323770 A1 | 11/1993 |
| WO | WO9428882 A1 | 12/1994 |
| WO | WO9816206 A1 | 4/1998 |
| WO | WO9851287 A1 | 11/1998 |
| WO | WO9912524 A1 | 3/1999 |
| WO | WO0137817 A1 | 5/2001 |
| WO | 02/30398 A2 | 4/2002 |
| WO | 0230398 | 4/2002 |
| WO | 0230398 A2 | 4/2002 |
| WO | WO0230398 A2 | 4/2002 |
| WO | 03013538 A1 | 2/2003 |
| WO | 2003013476 A1 | 2/2003 |
| WO | WO03009846 A1 | 2/2003 |
| WO | 03086364 A1 | 10/2003 |
| WO | WO04000825 A1 | 12/2003 |
| WO | 200402418 A2 | 3/2004 |
| WO | 2004024128 | 3/2004 |
| WO | 2004050023 A2 | 6/2004 |
| WO | 2004056354 A1 | 7/2004 |
| WO | WO04056354 A1 | 7/2004 |
| WO | 2005021009 A2 | 3/2005 |
| WO | 2005032474 | 4/2005 |
| WO | 2005065661 A2 | 7/2005 |
| WO | 2005097075 | 10/2005 |
| WO | 2005097075 A2 | 10/2005 |
| WO | 2005099674 A1 | 10/2005 |
| WO | 2006011592 | 2/2006 |
| WO | 2006017336 A2 | 2/2006 |
| WO | 2006085335 A2 | 8/2006 |
| WO | 2007082770 A1 | 7/2007 |
| WO | 2008122993 A1 | 10/2008 |
| WO | 2009113061 A1 | 9/2009 |
| WO | 2010044842 A1 | 4/2010 |
| WO | 2012002644 A2 | 1/2012 |

OTHER PUBLICATIONS

Merriam-Webster Online Dictionary, http://www.meriam-webster.com/dictionary/cure, obtained online Dec. 16, 2009.*

Andersson et al., J. Pharmacuetical and Biomedical Analysis, 2000, 22, 325-339.*

Torpac, Capsul Size Chart, 2000, pp. 1-3.

Supplemental European Search Report Prepared by Miralles J. Gimenez dated Aug. 23, 2012.

Supplemental European Search Report Prepared by Antonio Raposo dated Aug. 2, 2012.

Paste, http://www.thefreedictionary.com/paste,accessed Jun. 29, 2012.

Paste, www.thefreedictionary.com/paste, accessed Jun. 26, 2012.

Anderson, M. et al., Analysis of Film Coating Thickness and Surface Area of Pharmaceutical Pellets using Fluorescence Microscopy and Image Analysis, J. Pharmaceutical and Biomedical Analysis, (2000), vol. 22, pp. 325-339.

Arora, S. et al, Pulsatie Drug Delivery Systems: An Approach for Controlled Drug Delivery, Indian J. Pharm. Sci., (2006), vol. 68, pp. 295-300.

Aulton, M. E.—The science of dosage form design, (1988), pp. 316-321, (Churchill Livingstone Ed.), Pharmaceutics.

Banga, A. et al., "Incorporation of Simethicone into Syrup or Clear Base Liquid Orals", Drug Development and Industrial Pharmacy, (1989), vol. 15(5), pp. 671-704.

Conner, A. L. et al., A Scintigraphic Study to Investigate the Potential for Altered Gut Distribution of Loperaminde from a Loperaminde-Simethicone Formation in Man, European Journal of Pharmaceutical Sciences, (2001), vol. 13, pp. 369-374.

Dashevsky, A. etal., PH-independent Release of Baisc Drug from Pellets Coated with the Extended Release Polymer Dispersion Kollicoat® SR 30 D and the Enteric Polymer Dispersion Kollicoat® MAE 30 DP, European Journal of Pharmaceutics and Biopharmaceuticals, (2004), vol. 58, pp. 45-49 (available online Jun. 1, 2004).

Deshpande, A. et al., Development of a Novel Controlled-Release System for Gastric Retention, Pharmaceutical Research, (1997), vol. 14, No. 6, pp. 815-819.

Krögel, I. et al., Floating of Pulsatile Drug Delivery Systems Based on Coated Efferescent Cores, International of Pharmaceutics, (1999) vol. 187, pp. 175-184 anl.

Laizure, S. C. et al., Stability of Bupropion and its Major Metabolites in Human Plasma, Therapeutic Drug Monitoring (1985), vol. 7 (4); p. 447.

Lehmann, K. et al.,—Fast Disintegrating Controlled Release Tablets from Coated Particles—Drugs Made in Germany, (1994) vol. 37, No. 2, pp. 53-60.

(56) References Cited

OTHER PUBLICATIONS

Martindale, The Extra Pharmacopoeia, 30th Ed. (The Pharmaceutical Press, London 1993).
Rakur, G. et al., 2-((2-Pyridylm-ethyl) Sulfiny) Benzimidazoles: Acid Sensitive Suicide Inhibitors of the Proton Transport System in the Parietal Cell, Biochem Biophys. Res. Comm. (1985), vol. 128, No. 1, pp. 477-484.
Remington's Pharmaceutical Sciences, 18th ed, (1990), Chapter 83, pp. 1539-1540.
Sathe, P.M. et al, Drug Product Performance, In Vitro, Generic Drug Product Development, (2004), vol. 143, Chapter 8, pp. 187-209.
Steward, P.A. Review of Pharmaceutical Controlled Release Method and Devices, (1995) 12 pages.
Sungthongjeen, S. et al.,—Development of Pulsatile Release Tablets with Swelling and Rupturable Layers, Journal of Controlled Release, (2004), vol. 95, pp. 1147-1159.
Sunshine, et al., "Analgesic Efficacy of Pentazocine Versus a Pentazocine-Naxloxone Combination Following Oral Administration", Clin. J. Pain, (1988), vol. 4, pp. 35-40.
Venkatraman et al., Chapter 22, An overview of Controlled Release Systems, Handbook of Pharmaceutical Controlled release Technology by Donald Wise, Published, (2002) p. 443.
Walters, S. M., Influence of pH on Hydrolytic Decomposition of Dimethylpropion Hydrochloride: Stability Studies on Drug Substance and Tables using High-Performance Liquid Chromatograph, J. Pharma Science, (1980), vol. 69 (10), p. 1208.
Wang, R. et al., Crossover and Parallel Study of Oral Analgesics, J. Clin. Pharmacl., (1981) Vo. 21, pp. 162-168.
Merriam-Webster Online Dictionary, http://www.meriam-webster.com/dictionary/prevent, obtained online Feb. 18, 2008.
European Patent Application No. 04 737 76.2-2112, Examination Report dated Nov. 18, 2009.
Office Action for U.S. Appl. No. 10/561,700 dated Dec. 27, 2007.
Office Action for U.S. Appl. No. 10/561,700 dated Mar. 18, 2008.
Office Action for U.S. Appl. No. 10/561,700 dated Apr. 17, 2009.
Office Action for U.S. Appl. No. 10/561,700 dated Sep. 3, 2009.
Office Action for U.S. Appl. No. 10/861,809 dated Sep. 28, 2009.
Office Action for U.S. Appl. No. 10/861,809 dated Nov. 26, 2008.
Office Action for U.S. Appl. No. 10/861,809 dated Nov. 13, 2007.
Office Action for U.S. Appl. No. 12/092,654 dated Mar. 12, 2010.
Office Action for Canadian Patent Application No. 2,626,558 dated Nov. 25, 2009.
English translation of Office Action dated Oct. 13, 2010 corresponding to Chinese Patent Application No. 200780019372.7.
International Search Report and Written Opinion; PCT/CA2007/000540.
International Search Report and Written Opinion; PCT/CA2007/000548.
International Search Report and Written Opinion; PCTCA2007/000550.
International Search Report and Written Opinion; PCT/CA2007/000862.
International Search Report and Written Opinion dated Aug. 31, 2007; PCT/CA2007/000862.
International Preliminary Report on Patentability dated Nov. 27, 2008; PCT/CA2007/000862.
International Preliminary Examination Report; PCT/CA2002/01360.
International Search Report; PCT/CA2002/01360.
International Search Report; PCT/CA2002/00054.
International Search Report and Written Opinion; PCT/CA2004/000825.
Encyclopaedia of Polymer Science and Technology; vol. 10 (1969); published by John Wiley & Sons.
U.S. Appl. No. 11/473,386.
U.S. Appl. No. 09/947,464.
U.S. Appl. No. 10/561,700.
U.S. Appl. No. 12/696,118.
U.S. Appl. No. 12/225,956.
U.S. Appl. No. 12/225,954.
U.S. Appl. No. 11/432,226.
U.S. Appl. No. 12/092,654.
U.S. Appl. No. 10/924,649.
U.S. Appl. No. 10/900,415.
U.S. Appl. No. 10/880,474.
U.S. Appl. No. 11/315,868.
Canadian Intellectual Property Office, Office Action dated Nov. 15, 2013 in CA application 2,579,382, 2 pages.
Canadian Intellectual Property Office, Office Action dated Dec. 4, 2013 in CA application 2,648,278, 3 pages.
European Patent Office, Examination Report dated Sep. 24, 2013 for EP application 07 719 478.5-1455, 6 pages.
Super Disintegrants: Characterization and Function (From European Examination Report of #3 above), 2007 by Informa Healthcare USA, Inc., 18 pages.
International Search Report from PCT/CA2013/000610; dated Sep. 18, 2013; Prepared by Nasreddine Slougui on Sep. 13, 2013.
Ganesh Rasve, et al.; Pulsatile Drug Delivery System: Current Scenario; International Journal of Pharma and Bio Sciences; vol. 2 / Issue 3/ Jul.-Sep. 2011; 12 pages.
Merrian-Webster Dictionary; definition of "Paste"; 1 page, accessed Dec. 16, 2014.
Buhse, Lucinda, et al. "Topical drug classification." international journal of pharmaceutics 295 (2005): 101-112.
Canadian Examination Search Report, 50 rue Victoria, Place du Portage 1, Gatineau Quebec K1A OC9; dated Sep. 29, 2017. 4 pages, U.S. Pat. No. 2,648,278.

* cited by examiner

PULSED EXTENDED-PULSED AND EXTENDED-PULSED PULSED DRUG DELIVERY SYSTEMS

FIELD OF THE INVENTION

The present invention is directed to a drug delivery engine which provides an extended-pulsed pulsed or pulsed extended-pulsed controlled release delivery of active pharmaceutical ingredient(s) APIs, and more specifically to the superior and precise control of the release of API to the gastrointestinal tract and plasma whereby the shape, number, magnitude, position and chronological separation of the plasma concentration peaks (maxima), troughs (minima) and plateaus and their inter relations can be determined and controlled precisely. In particular, the present invention relates to a better once daily dosing of a medication in a unitary dosage form designed to mimic desirable in-vivo characteristics of multiple dosing per day regimen. The dosage forms can be formulated to initially provide extended release followed by one or more pulses of drug release or initially to provide one or more pulses of drug release followed by extended release. It may also be formulated to initially provide one or more pulses of drug release and optionally followed by an extended release and one or more pulses of drug release. The rate, extent and time of the pulses are controlled precisely.

The dosage forms and methods of the present invention are particularly suitable for the administration of APIs, their bases, salts, metabolites, pro-drugs, racemates, enantiomers, optical isomers, related substances or a mixture thereof.

The ability to precisely control the shape, number, magnitude, position and timing of the plasma concentration peaks (maxima), troughs (minima) and plateaus and their inter relations, provides for better tolerance, reduced abuse potential, reduced side effects, and improved treatment compliance. This approach to drug delivery is far more superior and represents a paradigm shift from the current practice whereby delivery systems are designed only with the intention to control bioavailability and maximum concentration of drug in plasma.

BACKGROUND OF THE INVENTION

It is well known in the art that extended release dosage forms are used to control the release of pharmaceutically active ingredients. These devices operate successfully for their intended use. However, these devices are often limited in their use to deliver pharmaceutical active ingredients in a pulsatile manner. These devices are also limited in their ability to mimic precisely the desirable in-vivo characteristics that multiple dosing per day regimen presents i.e., the ability to "switch on and switch off", or provide pulsed or multiple peaks, troughs and plateau of drug concentration at predetermined time or time interval while still maintaining control on the rate and extent of drug input.

It will be appreciated by those versed in the art, that if a device can be provided that allows the delivery of pharmaceutically active ingredients their bases, salts, metabolites, pro-drugs, racemates, enantiomers, optical isomers, related substances or a mixture thereof in such a way that the shape, number, magnitude, position and timing of the plasma concentration peaks (maxima), troughs (minima) and plateaus and their inter relations can be controlled precisely such a device would have a positive value and represent an advancement in the science of controlled delivery technology. The present invention is directed to these, as well as other, significant outcome.

SUMMARY OF THE INVENTION

The present invention provides, in one embodiment, a therapeutic composition in a device for the oral administration of APIs, the device consist of one or more unit dosage forms consisting of a core loaded with up to 1000 mg of API and up to 1000 mg of a super disintegrant, the API loaded core is coated with a delayed release coat as first coat and a second coat loaded with up to 1000 mg of API and optionally a third coat consisting of a delayed release coat or optionally a third coat and fourth coat consisting of a delayed release coat and coat loaded with up to 1000 mg of API respectively.

In another embodiment, there is presented a therapeutic composition in a device for the oral administration of APIs, the device consist of one or more unit dosage forms containing up to 1000 mg of API and up to 1000 mg of one or more super disintegrant, in an extended release polymeric or waxy matrix and one or more unit dosage forms of immediate release core loaded with up to 1000 mg of API and up to 1000 mg of one or more super disintegrant, and/or one or more units consisting of a core loaded with up to 1000 mg of API and up to 1000 mg of one or more super disintegrant, coated with a delayed release coat.

In yet another embodiment, there is presented a therapeutic composition in a device for the oral administration of APIs, the device consist of one or more unit dosage forms containing up to 1000 mg of API and up to 1000 mg of one or more super disintegrant, in an extended release polymeric or waxy matrix surrounded by one or more coat loaded with up to 1000 mg of API, and optionally one or more units containing up to 1000 mg of API and up to 1000 mg of one or more super disintegrant, in an extended release polymeric or waxy matrix surrounded by one or more coat loaded with up to 1000 mg of API, and coated with a delayed release coat.

In further embodiment, there is presented a therapeutic composition in a device for the oral administration of APIs, the device consist of one or more unit dosage forms containing up to 1000 mg of API and up to 1000 mg of one or more super disintegrant, in a core surrounded by a non aqueous but organosoluble polymeric coat and optionally one or more coat loaded with up to 1000 mg of API, and optionally one or more units containing up to 1000 mg of API and up to 1000 mg of one or more super disintegrant, in a core surrounded by a non aqueous but organosoluble polymeric coat surrounded by one or more coat loaded with up to 1000 mg of API, and coated with a delayed release coat and optionally one or more units containing up to 1000 mg of API and up to 1000 mg of one or more super disintegrant, in a core.

Some embodiments of the current invention have cores which contain from 0 to 1000 mg of bases such as sodium bicarbonate, sodium carbonate, potassium bicarbonate, potassium carbonate and from 0 to 1000 mg of acids such as citric acid, malic acid, adipic acid, tartaric acid and fumaric acid. The bases and acids may be in direct contact or separated by a physical or chemical barrier.

The device may be designed to provide an initial release of aliquot amount of the API, followed by one or more pulsed and or an extended pulsed release delivery of additional aliquot amount of API at predetermined times resulting in one or more plasma concentration peaks and/or troughs. They may also be designed to provide extended pulsed release of aliquot amount of the API, followed by one or more pulsed delivery of additional aliquot amount of API at predetermined times resulting in one or more plasma concentration peaks and/or troughs. In another design, the device provides an extended pulsed release of aliquot amount of the API, resulting in one or more plasma concentration peaks and/or troughs and/plateaus. In yet other designs, the device may yield a pulsed pulsed-extended release profile; an extended-pulsed release profile; a multi pulsed release profile; a delayed multi-pulsed release profile; a delayed extended-pulsed release profile; a delayed pulse on, pulse off and pulse on release profile; a pulse on, pulse off and pulse on release profile or a combination there of.

In such embodiments, it is most preferred that the ratio of the plasma concentration values of any one peak (maxima) to any one trough (minima) or plateau is from about 25% to 400%. It is also preferred that the ratio of the plasma concentration values of a peak (maxima) to the next trough (minima) or plateau is from about 25% to 400%. It is further preferred that the ratio of the plasma concentration values of a trough (minima) or plateau to the next peak (maxima) is from about 25% to 400%. In the embodiments taught by this invention it is preferred that the coats on an individual basis are applied to yield a weight gain of up to 500% and surface area of up to 80 mg per cm$^2$. In a further aspect of the embodiments it may be preferable to have a lag phase before the onset of release of API.

In a preferred embodiment, the amount of doses, the separation of doses and the rate of input of API is used to control the release profile and the chronological separation of doses, maxima, minima or plateau in vivo.

BRIEF DESCRIPTION OF THE DRAWINGS

The various types of in vivo release profile and chronological separation of doses, maxima, minima or plateau will be further illustrated by the following in vivo schematics thereof, given by way of example only with reference to the accompanying drawings in which.

DETAILED DESCRIPTION OF THE PREFERRED EMBODIMENTS

Figure 1:
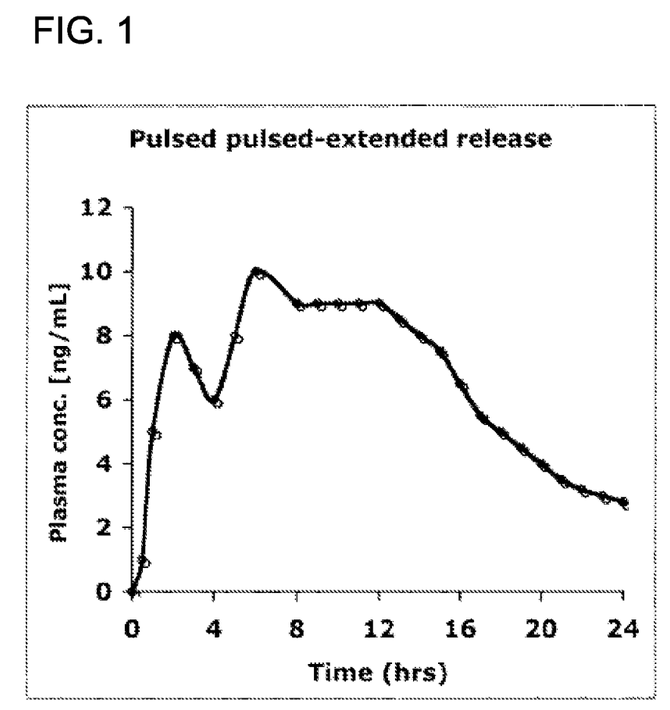
FIG. 1 is a schematic of an in vivo time-concentration profile for a variation of certain preferred dosage forms in accordance with the invention depicting pulsed pulsed-extended release profile.
Figure 2:
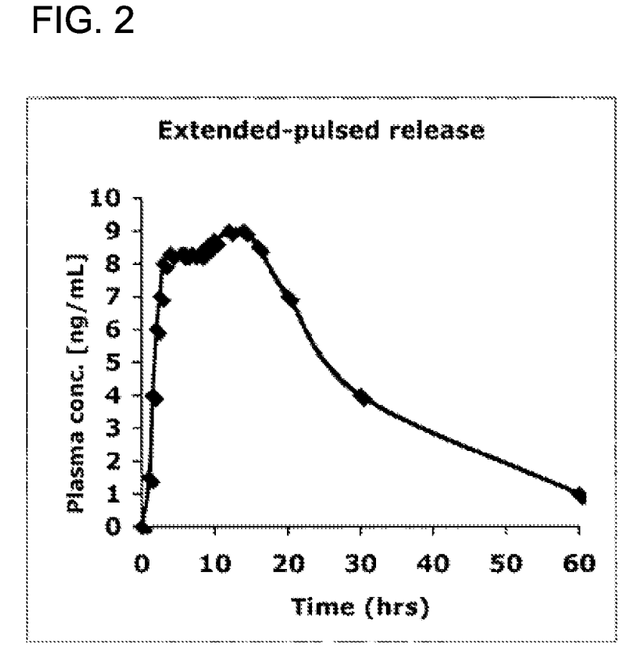
FIG. 2 is a schematic of an in vivo time-concentration profile for a variation of certain preferred dosage forms in accordance with the invention depicting extended-pulsed release profile.
Figure 3:
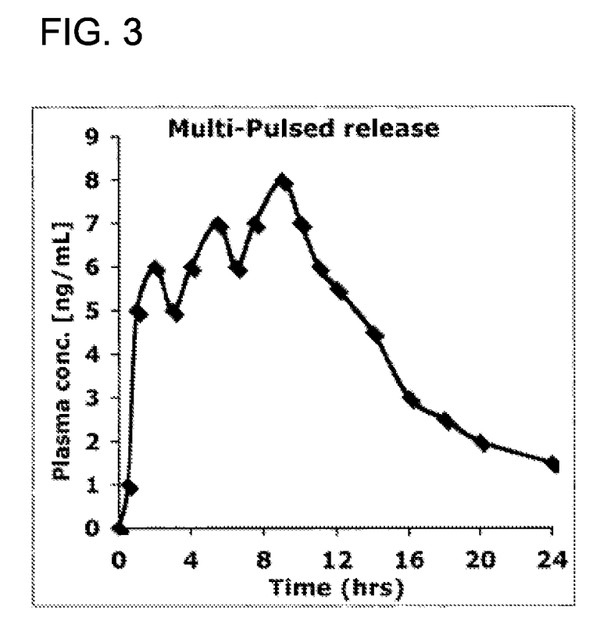
FIG. 3 is a schematic of an in vivo time-concentration profile for a variation of certain preferred dosage forms in accordance with the invention depicting multi pulsed release profile.
Figure 4:
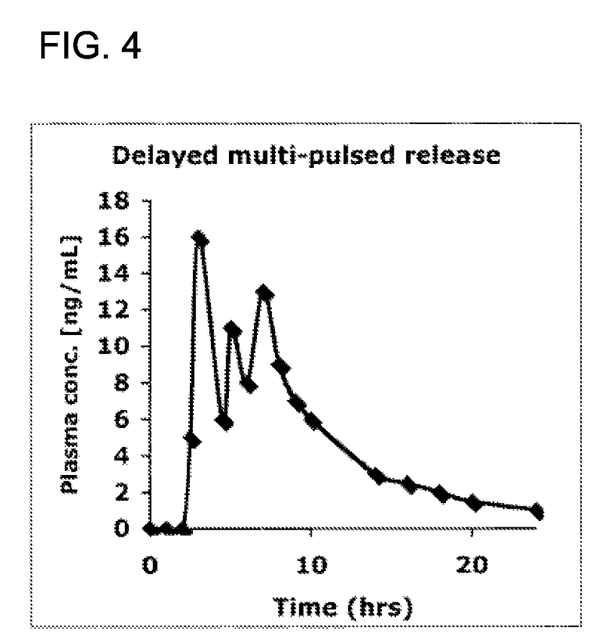
FIG. 4 is a schematic of an in vivo time-concentration profile for a variation of certain preferred dosage forms in accordance with the invention depicting delayed multi-pulsed release profile.
Figure 5:
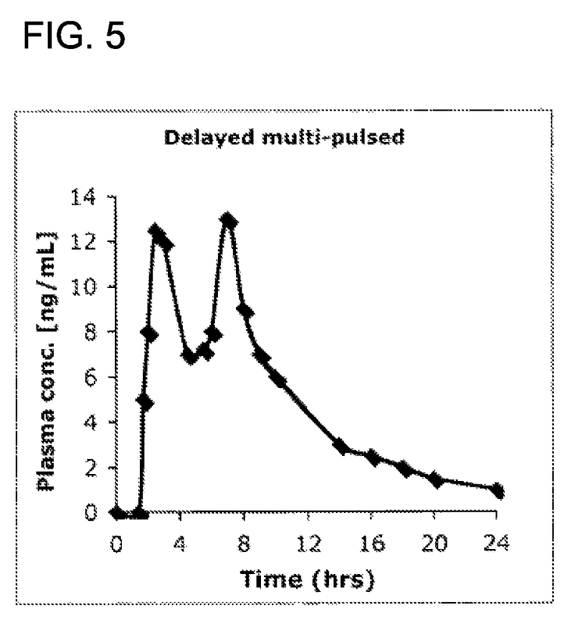
FIG. 5 is a schematic of an in vivo time-concentration profile for a variation of certain preferred dosage forms in accordance with the invention depicting another type of delayed multi-pulsed release profile.
Figure 6:
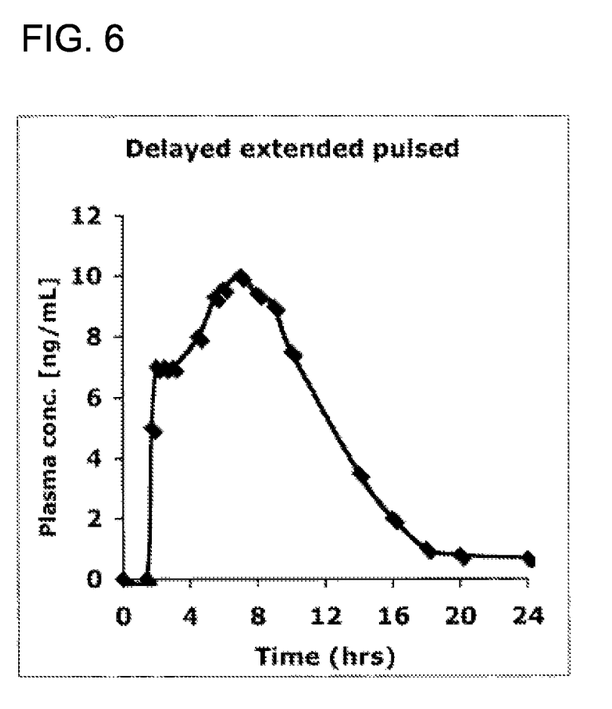
FIG. 6 is a schematic of an in vivo time-concentration profile for a variation of certain preferred dosage forms in accordance with the invention depicting delayed extended-pulsed release profile.
Figure 7:
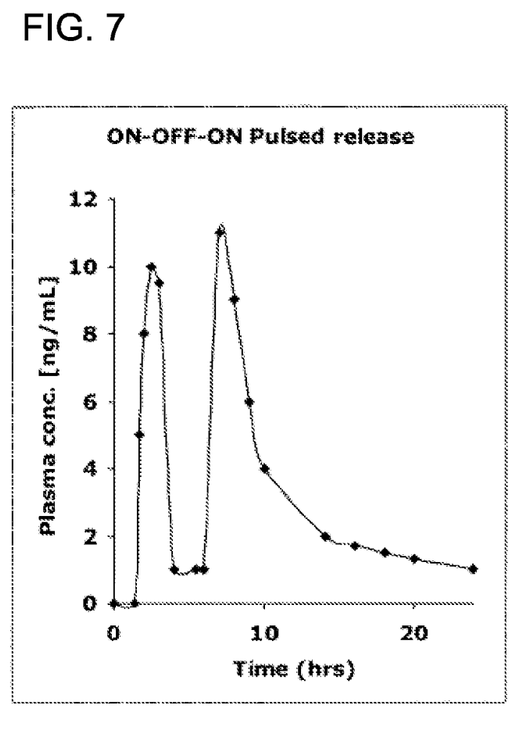
FIG. 7 is a schematic of an in vivo time-concentration profile for a variation of certain preferred dosage forms in accordance with the invention depicting delayed pulse on, pulse off and pulse on release profile.

The invention comprises a variety of therapeutic compositions contained within a device or housing such as a chamber or reservoir. Each unit dosage form or population of composition contained within the housing can be made into a variety of different vehicles such as granules, beads, pellets, or tablets.

Each vehicle in one aspect consists of a core containing the agent to be delivered, a disintegrant, and optionally a bases and an acid. The cores may be coated with the agent and or delayed release coat. The core may contain a polymeric material in a matrix. A variety of the different types of vehicles may be packed into a housing. The housing may also additionally comprise the agent to be release in powdered, crystalline or granule form.

The vehicles as made into granules, beads, pellets or tablets can be further fabricated to be regular or irregular in shape and preferably have a diameter and thickness of up to about 40 mm, and preferably up to about 20 mm and most preferably up to about 13 mm.

The polymer(s) for use in making the different vehicles of pharmaceutical formulations may be selected from any polymers which are soluble or insoluble in water and can retard the release especially those which can form hydrocolloids. They include naturally occurring or synthetic, anionic or nonionic, hydrophilic rubbers, starch derivatives, cellulose derivatives, polysaccharides, carbomer, proteins, and the like. Specific examples are acacia, tragacanth, Xanthan gum, locust bean gum, guar-gum, karaya gum, pectin, alginic acid, polyethylene oxide, polyethylene glycol, propylene glycol alginate, hydroxypropyl methylcellulose, methylcellulose, hydroxypropyl cellulose, hydroxyethyl cellulose, carboxymethylcellulose sodium, polyvinylpyrrolidone, carboxyvinyl polymer, sodium polyacrylate, alpha starch, sodium carboxymethyl starch, albumin, dextrin, dextran sulfate, agar, gelatin, casein, sodium casein, pullulan, polyvinyl alcohol, deacetylated chitosan, polyethyoxazoline, poloxamers, ethylcellulose, chitin, chitosan, cellulose esters, aminoalkyl methacrylate polymer, anionic polymers of methacrylic acid and methacrylates, copolymers of acrylate and methacrylates with quaternary ammonium groups, ethylacrylate methylmethacrylate copolymers with a neutral ester group, polymethacrylates, surfactants, aliphatic polyesters, zein, polyvinyl acetate, polyvinyl chloride, cellulose esters, cellulose ethers, polyethylene oxide, carbomer, cyclodextrins, polyethelene glycol, dextran, polyvinylpyrrolidone, lactide/glycolide copolymers, poly(ortho esters), polyanhydrides, polyvinyl alcohol, alginates, polysaccharides, polyamides, polyvinyl chloride, polyethylene vinyl acetate, polvinyl pyrrolidone, polyurethanes, hydrogels, silicone polymers, polyacrylates, polymethacrylates, polyanhydrides, poly amino carbonates, deacetylated chitin, collagen, polyisobutylenes, gelucire, glyceryl behenate and the like.

The super-disintegrant that may be formulated into the compositions of the invention may be selected from the group consisting of sodium starch glycolate, sodium croscarmellose, homopolymer of cross-linked N-vinyl-2-pyrrolidone, and alginic acid and the like and mixtures thereof.

The delayed release coat for use in the compositions of the invention may be selected from shellac, polyvinyl acetate phthalate (PVAP), hydroxypropylmethyl-cellulose acetate succinate (HPMCAS), cellulose acetate phthalate (CAP), methacrylic acid copolymer, hydroxy propyl methylcellulose succinate, cellulose acetate succinate, cellulose acetate hexahydrophthalate, hydroxypropyl methylcellulose hexahydrophthalate, hydroxypropyl methylcellulose phthalate (HPMCP), cellulose propionate phthalate, cellulose acetate maleate, cellulose acetate trimellitate, cellulose acetate butyrate, cellulose acetate propionate, methacrylic acid/methacrylate polymer, methacrylic acid-methyl methacrylate copolymer, ethyl methacrylate-methylmethacrylate-chlorotrimethylammonium ethyl methacrylate copolymer, natural resins, Sandarac, copal collophorium and the like and mixtures thereof.

The bases for use in the compositions of the invention may be selected from sodium bicarbonate, sodium carbonate, potassium bicarbonate, potassium carbonate.

The acids for use in the compositions of the invention may be selected from citric acid, malic acid, adipic acid, tartaric acid and fumaric acid.

Each composition may be formulated into a variety of different vehicles such as for example granules, beads, pellets, or tablets which may also contain surfactants, excipients and mixtures thereof in amounts that are readily determined by one of skill in the art.

The vehicle(s) of the invention may include a variety of active agents such as for example pharmaceuticals, chemicals, biologicals, pesticides, insecticides, algicides, fungicides, germicides and herbicides, their metabolites, prodrugs, racemates, enantiomers, optical isomers, salts, bases, related substances or a mixture thereof.

In one preferred aspect, the active agent comprises Acetaminophen/Codeine, Albuterol, Alendronate, Allopurinol, Alprazolam, Amtriptyline, Amlodipine, Amlodipine/Benazepril, Amoxicillin, Amoxicillin/Clavulanate, Amphetamine Mixed salts, acarbose, Atelolol, Atorvastatin, Azithromycin, Beclomethasone, Benazepril, Bisoprolol/HCTZ, Brimonidine, Calcitonin Salmon, Carbamazepine, Carisoprodol, Carvedilol, cefprozil, Cefuroxime, Clecoxib, Cephalexin, Cetinzine, Ciprofloxacin, Cisapride, Citalopram, Clarithromycin, Clonazepam, Klondike, Clopidogrel, Clotrimazole/Betamethasone, Cyclobenzaprine, Diazepam, Misoprostol, Digoxin, Divalproex, Donepezil, Doxazosin, Enalapril, Erythromycin, Estradiol, Ethinyl Estradiol/Norethindrone, Famotidine, Felodipine, Fexofenadine, Fexofenadine/Pseudoephedrine, Fluoxetine, Fluticasone Propionate, Fluvastatin, Fluvoxamine maleate, Fosinopril, Furosemide, Gemfibrozil, Glimepiride, Glyburide, Guaifenesin/Phenylpropanolamine, Granisetron HCl, Hydrochlorothiazide, Hydrocodone w/APAP, Ibuprofen, Ipratropium, Ipratropium/Albuterol, Irbesartan, Isosorbide Mononitrate, Lansoprazole, Latanoprost, Levofloxacin, Levonorgestrel/Ethinyl Estradiol, Levothyroxine, Lisinopril, Lisinopril/HCTZ, Loratadine, Loratidine/Pseudoephedrine, Lorazepam, Losartan, Losartan/HCTZ, Lovastatin, Methylprednisolone, Methylphenidate or its optical isomers, Metoprolol, mightol Mometasone, Montelukast, Mupirocin, Naproxen, Nitrofurantoin, Nizatidine, Olanzapine, Oxaprozin, Oxycodone, Oxycodone/APAP, Paroxetine, Penicillin VK, Phenytoin, Potassium, Chloride, Pramipexole HCl, Pravastatin, Prednisone, Promethazine, Propoxyphene N/APAP, Propranolol, Quinapril, Raloxifene, Ramipril, Ranitidine, repaglinide, Risperidone, Rofecoxib, Salmeterol, Sertraline, Sildenafil Citrate, Simvastatin, Sumatriptan, Tamoxifen, Tamsulosin, Tamazepam, Terazosin, Terbinafine, Tobramycin/Dexamethasone, Tolterodine, Tranylcypromine sulfte, Trazodone, Triamterene/HCTZ, Troglitazone, Valsartin, Venlafaxin, Warfarin, Zafirlukast and Zolpidem.

In a further embodiment the active agent comprises one or more of the drugs used in HIV or AIDS treatment such as for example Abacavir, amprenavir, stavudine, zalcitabine, didanosine, delavirdine, efavirenz Hydroxyurea, indinavir, lamivudine, lopinavir, nelfinavir, nevirapine, ritonavir, Saquinavir, stavudine and zidovudine.

In yet another embodiment, the active agent comprises one or more proteins, peptides, hormones, prostaglandins, and anticancer agents.

The unit dosage forms present in the controlled release delivery device in accordance with the present invention may be manufactured using conventional granulation, pelletization, tabletting and/or coating technologies. As an example, a homogeneous blend of the pharmaceutically active substance, disintegrant, and excipients are granulated, dried, milled, lubricated, blended and pressed into tablets or pellets. Alternatively, the homogeneous blend is granulated, extruded and dried. Other populations of vehicles are manufactured by powder/solution layering on non pareils or inert pharmaceutical spheres.

A complete or partial coating may be applied on one or more of the vehicle populations by spraying, molding and/or dipping. Finally, the various population of vehicles in the form of granules, beads, pellets and tablets are assembled in no particular order within a housing such as a chamber chamber/reservoir.

In accordance with the present invention the housing that forms the chamber or reservoir for encapsulating the various vehicles comprising the different pharmaceutical formulations therein may additionally contain a non-toxic metal or metal alloy such as for example titanium, platinum and gold The housing may also contain non-toxic plastic, hard gelatin or hydroxypropyl methyl cellulose.

The device of the invention is suitable for oral ingestion as well as via sublingual, intraocular, intramuscular, subcutaneous, anal and vaginal use as well as for implantation to a desired location within the body. The device of the present invention can be used for a variety of different applications including for human and veterinary use and agricultural use.

The controlled release drug delivery system as taught in the preset invention provides a novel device in which a housing has incorporated therein a variety of different compositions in the form of pellets, granules, beads and tablets that each may provide a different dose, rate of input of a dose, chronological separation of doses, maxima, minima or plateau used for the unexpected and unobvious but precise delivery of similar, dissimilar or incompatible substances in a pulsatile manner in the environment of use.

Oil components may also be used in the current invention. These include oils and fats, waxes, hydrocarbons, higher fatty acids, higher alcohols, esters, metal salts of higher fatty acids, and the like. Specific examples of oils and fats include plant oils, e.g. cacao butter, palm oil, Japan wax (wood wax), coconut oil, etc.; animal oils, e.g. beef tallow, lard, horse fat, mutton tallow, etc.; hydrogenated oils of animal origin, e.g. hydrogenated fish oil, hydrogenated whale oil, hydrogenated beef tallow, etc.; hydrogenated oils of plant origin, e.g. hydrogenated rape seed oil, hydrogenated castor oil, hydrogenated coconut oil, hydrogenated soybean oil, etc.; and the like. Of these hydrogenated oils are preferred as an oil component of the present invention. Specific examples of waxes include plant waxes, e.g. carnauba wax, candelilla wax, bayberry wax, auricurry wax, espalt wax, etc.; animal waxes, e.g. bees wax, breached bees wax, insect wax, spermaceti, shellac, lanolin, etc.; and the like. Of these preferred are carnauba wax, white beeswax and yellow beeswax. Paraffin, petrolatum, microcrystalline wax, and the like, are given as specific examples of hydrocarbons, with preferable hydrocarbons being paraffin and microcrystalline wax. Given as examples of higher fatty acids are caprilic acid, undecanoic acid, lauric acid, tridecanic acid, myristic acid, pentadecanoic acid, palmitic acid, malgaric acid, stearic acid, nonadecanic acid, arachic acid, heneicosanic acid, behenic acid, tricosanic acid, lignoceric acid, pentacosanic acid, cerotic acid, heptacosanic acid, montanic acid, nonacosanic acid, melissic acid, hentriacontanic acid, dotriacontanic acid, and the like. Of these, preferable are myristic acid, palmitic acid, stearic acid, and behenic acid. Specific examples of higher alcohols are lauryl alcohol, tridecyl alcohol, myristyl alcohol, pentadecyl alcohol, cetyl alcohol, heptadecyl alcohol, stearyl alcohol, nonadecyl alcohol, arachyl alcohol, behenyl alcohol, carnaubic alcohol, corianyl alcohol, ceryl alcohol, and myricyl alcohol. Particularly preferable alcohols are cetyl alcohol, stearyl alcohol, and the like. Specific examples of esters are fatty acid esters, e.g. myristyl palmitate, stearyl stearate, myristyl myristate, behenyl behenate, ceryl lignocerate, lacceryl cerotate, lacceryl laccerate, etc.; glycerine fatty acid esters, e.g. lauric monoglyceride, myristic monoglyceride, stearic monoglyceride, behenic monoglyceride, oleic monoglyceride, oleic stearic diglyceride, lauric diglyceride, myristic diglyceride, stearic diglyceride, lauric triglyceride, myristic triglyceride, stearic triglyceride, acetylstearic glyceride, hydoxystearic triglyceride, etc.; and the like. Glycerine fatty acid esters are more preferable. Specific examples of metal salts of higher fatty acid are calcium stearate, magnesium stearate, aluminum stearate, zinc stearate, zinc palmitate, zinc myristate, magnesium myristate, and the like, with preferable higher fatty acid salts being calcium stearate and magnesium stearate. Polyethoxylated castor oil (cremaphor) is also useful.

These oil components and polymers can be used either singly or in combination of two or more. These are used in the following amounts, from about 1% to about 90% but preferably from about 1% to about 70%.

The drug loaded cores used in this invention can be made using extrusion spheronization techniques or by layering of drugs on sugar spheres, microcrystalline cellulose spheres, non pareil seeds or any pharmaceutically acceptable microspheres which are less than 3 mm in diameter.

Non drug loaded cores may be used in this invention to help provide homogeneity to ensure even distribution of the cores in the housing. Non drug loaded cores can be made using extrusion spheronization techniques. They can also be sugar spheres, microcrystalline cellulose spheres, non pareil seeds or any pharmaceutically acceptable microspheres which are less than 3 mm in diameter.

The drug loaded or non drug loaded cores that can be used range in size from about 1 micron to about 3000 microns in diameter and preferably from about 50 microns to about 1500 microns in diameter. From about 1% to about 100% and preferably from about 5% to about 100% of the drug loaded cores may be used in the housing. While from about 0% to about 90% and preferably from about 0% to about 70% of the non drug loaded cores may be used in the housing.

Pharmaceutical excipients such as diluents e.g., sugars, compression aids e.g., microcrystalline cellulose, surfactants e.g., sodium lauryl sulphate, surfactant micelles e.g., polyethoxylated castor oil (cremaphor), polymeric micelles e.g., amphiphilic block polymers (poloxamers), binders e.g., polyvinyl pyrolidone, glidants e.g., silicone dioxide, lubricants e.g., magnesium stearate etc. may be used in this invention. One skilled in the art will know what excipients to choose.

In one embodiment of the invention, the composite is prepared by embedding the drug loaded depots and optionally the non drug loaded depots in the release retarding polymer material and compressing to shape. This is accomplished by wet granulation to form wet granules and subsequent compression of the granules after they have been dried and lubricated.

In another embodiment, the dosage form can also be prepared by direct compression of a lubricated homogeneous blend of the drug loaded cores and optionally non drug loaded cores. In yet another embodiment excipients may be added to aid in granulation or compression etc. Another method of manufacture is by melt granulation.

In a further embodiment the dosage form is a layered tablet made by compression in a layer press. One layer is the release retarding layer and the other is an immediate release layer.

In yet another embodiment the release retarding layer is sandwiched between non release retarding layers.

EXAMPLES

The following examples are merely illustrative of the present invention and should not be considered limiting of the scope of the invention in any way. These examples and equivalents thereof will become more apparent to those skilled in the art in light of the present disclosure and the accompanying claims.

Example 1

Dexmethylphenidate Pulsed Release system.

Composition, manufacture and assembly of cores:

|  | Tablet I (%) | Tablet II (%) | Tablet III (%) |
| --- | --- | --- | --- |
| d-threo-methylphenidate hydrochloride | 32 | 32 | 16 |
| Hydroxypropyl methyl cellulose | — | 12 | — |
| sodium starch glycolate | 1 | — | 1 |
| Lactose | 45 | 40 | 61 |
| Silicone dioxide | 1 | 1 | 1 |
| Microcrystalline cellulose | 20 | 14 | 20 |
| Magnesium stearate | 1 | 1 | 1 |

Each tablet population is manufactured by wet granulation or dry granulation of a homogeneous blend of d-threo-methylphenidate hydrochloride+pharmaceutical necessities with exception of magnesium stearate. The wet granules are dried and passed through a comill. The resulting milled granules are lubricated with magnesium stearate and compressed into a preselected shape to for one population. A delayed release coat of the type that is pH reactive specifically EUDRAGIT® L (anionic copolymer) is applied onto Tablet population designated Tablet II to give a coverage of 4 mg per cm$^2$. A delayed release coat of the type that is pH reactive specifically EUDRAGIT® S (anionic copolymer) is applied onto Tablet population designated Tablet III to give a coverage of 6 mg per cm$^2$. Coating application is done in a perforated side vented coating pan. Finally, one tablet each from the three populations of tablets are assembled in no particular order in the holding chamber/reservoir made of hard gelatin or hydroxypropyl methyl cellulose.

Example 2

Duloxetine Delayed Pulsed Release System.
Composition, manufacture and assembly of cores:

|  | Beads I (mg) | Beads II (mg) |
| --- | --- | --- |
| Duloxetine hydrochloride | 200 | 200 |
| OPADRY ® II (pigmented PVA-based film coating formulation) | 50 | 50 |
| Sodium lauryl sulphate | 50 | 50 |
| Non pareil beads | 1200 | 120 |

Each duloxetine loaded bead population is manufactured by powder suspension layering of duloxetine hydrochloride unto non pareil beads in a fluid bed using top spray or bottom spray techniques. Duloxetine is suspended in OPADRY® II (pigmented PVA-based film coating formulation) aqueous suspension. A fluid set up for bottom spray is charged with non pareil beads. The duloxetine-OPADRY® II (pigmented PVA-based film coating formulation) suspension is sprayed unto the beads. A delayed release coat of the type that is pH reactive specifically EUDRAGIT® L (anionic copolymer) is applied onto the duloxetine loaded beads I to give a coverage of 4 mg per cm². An extended release coat, specifically a 50:50 ethylcellulose:hydroxypropyl methyl cellulose coat is applied to duloxetine loaded beads II to obtain a 4% weight gain. The extended release coated duloxetine loaded beads II is further coated with a delayed release coat of the type that is pH reactive specifically EUDRAGIT® L (anionic copolymer) to give a coverage of 4 mg per cm². These coats are applied in a fluid bed. Finally, the two populations of beads are assembled in a ratio of 1:3 (duloxetine coated beads I: duloxetine coated beads II) in the holding chamber/reservoir made of hard gelatin or hydroxypropyl methyl cellulose.

Example 3

Rivastigmine 12 mg Delayed Extended Pulsed Release System.
Composition, manufacture and assembly of cores:

|  | Spheroids I (mg) | Spheroids II (mg) |
| --- | --- | --- |
| Rivastigmine | 12 | 12 |
| Microcrystalline cellulose PH 101 | 388 | 388 |
| Water | qs | qs |

Each rivastigmine loaded bead population is manufactured by extrusion spheronization techniques. Rivastigmine is dissolved in water. Rivastigmine water solution is used to granulate microcrystalline cellulose in Hobart mixer. The wet granules are extruded in a Caleva extruder. The extrudate is charged into a Caleva spheroniser and spheronized to obtain rivastigmine loaded spheroids. The spheroids are dried to a loss of drying of less than 2%. A fluid set up for bottom spray is charged with spheroids I. A delayed release coat of the type that is pH reactive specifically EUDRAGIT® L (anionic copolymer) is applied onto the rivastigmine loaded spheroids I to give a coverage of 4 mg per cm². An extended release coat, specifically a 60:40 ethylcellulose:hydroxypropyl methyl cellulose coat is applied to rivastigmine loaded spheroids II to obtain a 4% weight gain. The extended release coated rivastigmine loaded beads II is further coated with a delayed release coat of the type that is pH reactive specifically EUDRAGIT® L (anionic copolymer) to give a coverage of 4 mg per cm². These coats are applied in a fluid bed. Finally, the two populations of beads are assembled in a ratio of 1:3 (rivastigmine coated spheroids 1: rivastigmine coated spheroids II) in the holding chamber/reservoir made of hard gelatin or hydroxypropyl methyl cellulose.

Example 4

Respiridone 6 mg Pulsed Extended Release system.
Composition, manufacture and assembly of cores:

|  | Tablet I (mg) | Tablet II (mg) |
| --- | --- | --- |
| Risperidone | 3 | 2 |
| Hydroxypropyl methyl cellulose | 12 | — |
| cross-linked N-vinyl-2-pyrrolidone | — | 2 |
| Lactose | 58 | 69 |
| Sodium lauryl sulphate | 5 | 5 |
| Silicone dioxide | 1 | 1 |
| Microcrystalline cellulose | 20 | 20 |
| Magnesium stearate | 1 | 1 |

Each tablet population is manufactured by wet granulation or dry granulation of a homogeneous blend of risperidone+pharmaceutical necessities with exception of magnesium stearate. The wet granules are dried and passed through a comill. The resulting milled granules are lubricated with magnesium stearate and compressed into a preselected shape to form one population. A delayed release coat of the type that is pH reactive specifically EUDRAGIT® L (anionic copolymer) is applied onto Tablet population designated Tablet II to give a coverage of 4 mg per cm². 1 mg of risperidone is blended into OPADRY® II (pigmented PVA-based film coating formulation) 15% (wt/wt) suspension in water. This suspension is used to coat the tablet population designated Tablet I. The risperidone OPADRY® II (pigmented PVA-based film coating formulation) suspension is prepared sufficient to apply a weight gain of 3% to the tablet. Coating application is done in a perforated side vented coating pan. Finally, one tablet each from the two populations of tablets are assembled in no particular order in the holding chamber/reservoir made of hard gelatin or hydroxypropyl methyl cellulose.

Example 5

Duloxetine 60 mg Pulsed Extended Release system.
Composition, manufacture and assembly of cores:

|  | Tablet I (mg) | Tablet II (mg) |
| --- | --- | --- |
| Duloxetine | 40 | 20 |
| Hydroxypropyl methyl cellulose | 30 | — |
| cross-linked N-vinyl-2-pyrrolidone | — | 4 |
| Lactose | 76 | 96.4 |
| Sodium lauryl sulphate | 10 | 10 |
| Silicone dioxide | 2 | 2 |
| Citric acid | — | 4 |
| Tartaric acid | — | 8 |
| Sodium bicarbonate | — | 13.6 |
| Microcrystalline cellulose | 40 | 40 |
| Magnesium stearate | 2 | 2 |

Each tablet population is manufactured by direct compression of a homogeneous blend of duloxetine+pharmaceutical necessities which has been lubricated with magnesium stearate. A delayed release coat of the type that is pH reactive specifically EUDRAGIT® L (anionic copolymer) is applied onto Tablet population designated Tablet I to give a coverage of 4 mg per cm². Tablet population designated Tablet II is not coated. Coating application is done in a perforated side vented coating pan. Finally, one tablet each from the two populations of tablets are assembled in no particular order in the holding chamber/reservoir made of hard gelatin or hydroxypropyl methyl cellulose Those skilled in the art will appreciate that diverse modifications, alteration, reconstruction and omissions in the system portrayed and described can be made without departing from the essence of the invention.

We claim:

1. A drug delivery device for oral administration of an active pharmaceutical ingredient (API), the device comprising:
   a) a first population of unit dosage forms comprising a core, wherein the core comprises the API and a super-disintegrant and wherein the first population of unit dosage forms is not coated;
   b) a second population of unit dosage forms comprising a core, wherein the core comprises the API and at least one of hydroxypropyl methyl cellulose and polyethylene oxide and wherein the second population of unit dosage forms comprises a pH-reactive coat; and
   c) a third population of unit dosage forms comprising a core, wherein the core comprises the API and a super-disintegrant and wherein the third population of unit dosage forms comprises a pH-reactive coat, wherein the API is d-threo-methylphenidate hydrochloride and is present in the first population in an amount of 32%, in the second population in an amount of 32% and in the third population in an amount of 16%.

2. The drug delivery device of claim 1, wherein the hydroxypropyl methyl cellulose is present in an amount of 12%.

3. The drug delivery device of claim 1, wherein the super-disintegrant is sodium starch glycolate.

4. The drug delivery device of claim 3, wherein the super-disintegrant is present in the first population in an amount of 1% and in the third population in an amount of 1%.

5. The drug delivery device of claim 1, wherein each of the first, second, and third populations further comprises lactose, silicone dioxide, microcrystalline cellulose, and magnesium stearate.

6. The drug delivery device of claim 5, wherein the silicone dioxide is present in each of the first, second, and third populations in an amount of 1%.

7. The drug delivery device of claim 5, wherein the magnesium stearate is present in each of the first, second, and third populations in an amount of 1%.

8. The drug delivery device of claim 5, wherein the microcrystalline cellulose is present in the first and third populations in an amount of 20% and in the second population in an amount of 14%.

9. The drug delivery device of claim 1, wherein the second population is coated to a coverage of 4 mg per cm2.

10. The drug delivery device of claim 1, wherein the third population is coated to a coverage of 6 mg per cm².

11. The drug delivery device of claim 1, comprising one member from each of the first, second, and third populations assembled within a holding chamber/reservoir made of hard gelatin or hydroxypropyl methyl cellulose.

12. The drug delivery device of claim 1, wherein the core of the second population of unit dosage forms comprises hydroxypropyl methyl cellulose.

13. A drug delivery device for oral administration of an active pharmaceutical ingredient (API), the device comprising:
   a) a first population of unit dosage forms comprising a core, wherein the core comprises the API and at least one of hydroxypropyl methyl cellulose and polyethylene oxide and wherein the first population of unit dosage forms comprises an immediate release coating comprising the API;
   b) a second population of unit dosage forms comprising a core, wherein the core comprises the API and a super-disintegrant and wherein the second population of unit dosage forms comprises a pH-reactive coat, wherein the API is risperidone and is present in the first population in an amount of 3% and in the second population in an amount of 2%.

14. The drug delivery device of claim 13, wherein 1 mg of the API is blended with the immediate release coating and applied to the first population of unit dosage forms to apply a weight gain of 3%.

15. The drug delivery device of claim 13, wherein the hydroxypropyl methyl cellulose is present in an amount of 12%.

16. The drug delivery device of claim 13, wherein the super-disintegrant is cross-linked N-vinyl-2-pyrrolidone.

17. The drug delivery device of claim 16, wherein the super-disintegrant is present in the second population in an amount of 2%.

18. The drug delivery device of claim 13, wherein each of the first and second populations further comprises lactose, sodium lauryl sulphate, silicone dioxide, microcrystalline cellulose, and magnesium stearate.

19. The drug delivery device of claim 18, wherein the silicone dioxide is present in each of the first and second populations in an amount of 1%.

20. The drug delivery device of claim 18, wherein the magnesium stearate is present in each of the first and second populations in an amount of 1%.

21. The drug delivery device of claim 18, wherein the microcrystalline cellulose is present in each of the first and second populations in an amount of 20%.

22. The drug delivery device of claim 18, wherein the sodium lauryl sulphate is present in each of the first and second populations in an amount of 5%.

23. The drug delivery device of claim 13, wherein the second population is coated to a coverage of 4 mg per cm².

24. The drug delivery device of claim 13, comprising one member from each of the first and second populations assembled within a holding chamber/reservoir made of hard gelatin or hydroxypropyl methyl cellulose.

25. The drug delivery device of claim 13, wherein the core of the first population of unit dosage forms comprises hydroxypropyl methyl cellulose.

26. A drug delivery device for oral administration of an active pharmaceutical ingredient (API), the device comprising:
   a) a first population of unit dosage forms comprising a core, wherein the core comprises the API and at least one of hydroxypropyl methyl cellulose and polyethylene oxide and wherein the first population of unit dosage forms comprises a pH-reactive coat;
   b) a second population of unit dosage forms comprising a core, wherein the core comprises the API, a super-disintegrant, an acid, and a base and wherein the second population of unit dosage forms is not coated, wherein the API is duloxetine and is present in the first population in an amount of 20% and in the second population in an amount of 10%.

27. The drug delivery device of claim 26, wherein the hydroxypropyl methyl cellulose is present in an amount of 15%.

28. The drug delivery device of claim 26, wherein the super-disintegrant is cross-linked N-vinyl-2-pyrrolidone.

29. The drug delivery device of claim 28, wherein the super-disintegrant is present in an amount of 2%.

30. The drug delivery device of claim 26, wherein the acid comprises citric acid and tartaric acid.

31. The drug delivery device of claim 30, wherein the citric acid is present in an amount of 2% and the tartaric acid is present in an amount of 4%.

32. The drug delivery device of claim 26, wherein the base is sodium bicarbonate.

33. The drug delivery device of claim 32, wherein the base is present in an amount of 6.8%.

34. The drug delivery device of claim 26, wherein each of the first and second populations further comprises lactose, sodium lauryl sulphate, silicone dioxide, microcrystalline cellulose, and magnesium stearate.

35. The drug delivery device of claim 34, wherein the silicone dioxide is present in each of the first and second populations in an amount of 1%.

36. The drug delivery device of claim 34, wherein the magnesium stearate is present in each of the first and second populations in an amount of 1%.

37. The drug delivery device of claim 34, wherein the microcrystalline cellulose is present in each of the first and second populations in an amount of 20%.

38. The drug delivery device of claim 34, wherein the sodium lauryl sulphate is present in each of the first and second populations in an amount of 5%.

39. The drug delivery device of claim 26, wherein the first population is coated to a coverage of 4 mg per $cm^2$.

40. The drug delivery device of claim 26, comprising one member from each of the first and second populations assembled within a holding chamber/reservoir made of hard gelatin or hydroxypropyl methyl cellulose.

41. The drug delivery device of claim 26, wherein the core of the first population of unit dosage forms comprises hydroxypropyl methyl cellulose.

* * * * *